(12) United States Patent
Lennhoff

(10) Patent No.: US 9,809,148 B2
(45) Date of Patent: Nov. 7, 2017

(54) EXTERNAL LIGHT MODULE FOR A VEHICLE

(75) Inventor: Ralf Lennhoff, Hagen (DE)

(73) Assignee: HUF HULSBECK & FURST GMBH & CO. KG, Velbert (DE)

( * ) Notice: Subject to any disclaimer, the term of this patent is extended or adjusted under 35 U.S.C. 154(b) by 51 days.

(21) Appl. No.: 13/338,718

(22) Filed: Dec. 28, 2011

(65) Prior Publication Data
US 2012/0170298 A1 Jul. 5, 2012

(30) Foreign Application Priority Data
Dec. 30, 2010 (DE) .................... 10 2010 061 643

(51) Int. Cl.
B60Q 1/00 (2006.01)
B60Q 1/26 (2006.01)
B60Q 1/32 (2006.01)

(52) U.S. Cl.
CPC ......... *B60Q 1/0023* (2013.01); *B60Q 1/2661* (2013.01); *B60Q 1/2665* (2013.01); *B60Q 1/2669* (2013.01); *B60Q 1/323* (2013.01); *B60Q 2400/40* (2013.01)

(58) Field of Classification Search
CPC ... B60Q 1/2661; B60Q 1/2665; B60Q 1/2669
USPC ....................................................... 362/501
See application file for complete search history.

(56) References Cited

U.S. PATENT DOCUMENTS

| | | | |
|---|---|---|---|
| 6,239,693 B1 * | 5/2001 | Benard et al. ........... 340/426.26 |
| 6,648,493 B2 * | 11/2003 | Klein ............................ 362/501 |
| 7,270,452 B2 * | 9/2007 | Wang ............................ 362/501 |
| 7,751,664 B2 * | 7/2010 | Ieda et al. ........................ 385/49 |
| 8,333,492 B2 * | 12/2012 | Dingman et al. ............. 362/501 |
| 8,523,412 B2 * | 9/2013 | Tanaka et al. ................. 362/501 |
| 8,579,481 B2 * | 11/2013 | Minter et al. ................. 362/501 |
| 2002/0172042 A1 | 11/2002 | Wen-Chung |
| 2004/0129040 A1 * | 7/2004 | Mathofer et al. .............. 70/208 |
| 2004/0184264 A1 | 9/2004 | Elam et al. |
| 2010/0077805 A1 * | 4/2010 | Mueller et al. .................. 70/91 |

FOREIGN PATENT DOCUMENTS

| | | |
|---|---|---|
| CN | 101646832 A | 2/2010 |
| DE | 19843594 A1 * | 4/2000 |
| EP | 2179890 A1 * | 4/2010 |
| WO | WO 2008120067 A2 * | 10/2008 |
| WO | 2008137634 A1 | 11/2008 |

OTHER PUBLICATIONS

Chinese Office Action dated Feb. 16, 2015 re: Application No. 2011104557839.

* cited by examiner

*Primary Examiner* — Alexander Garlen
(74) *Attorney, Agent, or Firm* — Cantor Colburn LLP

(57) ABSTRACT

An exterior assembly component for a vehicle and a manufacturing method thereof, where the component is in the form of an exterior mirror, door handle, door sill, skirt or similar, the component including a light module having at least one lamp emitting visible light toward the outside, and a plug to supply the lamp with electrical energy, where the light module represents a separate component of the assembly component which can be mounted on the assembly component and wherein the plug is designed as a single part with the a case of the light module.

23 Claims, 5 Drawing Sheets

EXTERNAL LIGHT MODULE FOR A VEHICLE

TECHNICAL FIELD

The invention relates to an external assembly component for a vehicle, in particular in the form of an exterior mirror, door handle, door sill, skirt or similar, having a light module comprising at least one lamp emitting a light visible to the outside. Furthermore, the invention also relates to a manufacturing procedure for an assembly component having a light module.

BACKGROUND

These kinds of assembly modules are known in the field of automotive engineering for any applications intended for instance to generate and emit light. Examples include headlights, tail lights, brake lights, turning signals etc. To increase the convenience with vehicles, so-called cove lighting is used as soon as darkness sets in, aimed at making it easier to find and get into the vehicle. In the process, it is also possible that the door handles used to open and get into the vehicle are additionally illuminated, for example by illuminating the recess underneath the door handle. Said illumination system can for instance be turned on when a person approaches the vehicle. In so doing, it may be necessary that the corresponding person is equipped with the appropriate ID transmitter for the cove lighting or all-around illumination of the vehicle to be turned on when it is dark. In addition, the illumination can also be turned on by means of an active action, such as for example by pushing a button of the radio-controlled ID transmitter used to activate the access control system.

A light module for a door handle has for instance been disclosed in the publication WO 2008/137634 A1, which enables recess illumination and cove lighting. Said light module is connected to a jack by means of flexible electrical wires, and the jack is used to connect the light module with the electronic system of the vehicle. The disadvantages of said exterior door handle are that the manufacture of the door handle with the light module is expensive because it consists of a plurality of individual parts which need to be connected with the door handle. Furthermore, the installation of the exterior door handle with the corresponding light module on the vehicle is also difficult, because the plug of the light module hanging on the flexible electrical supply cables first needs to be threaded through an opening in the sheet metal of the vehicle door before the door handle including the bearing bracket is pushed through this very same opening. Next, the corresponding plug of the light module needs to be connected with the mating connector inside the vehicle from the inside of the vehicle door. An additional installation step is required for this purpose.

BRIEF SUMMARY

The invention provides an external assembly component for a vehicle having a light module which can be manufactured easily on the one hand and installed easily in the vehicle on the other hand.

According to the invention, the light module of the assembly component represents a separate component of the assembly component which is attached to the assembly component and the plug is designed as a single piece with the light module, in particular the case of the light module. In the process, the plug is in particular designed with the same material and as a single piece together with the case of the light module. Because the plug is not connected with the light module by way of a flexible electrical supply cable as disclosed in the prior art, said electrical wire is not required. For this reason, the light module can be manufactured more economically and installed easier on the external assembly component. In addition, the assembly component itself together with the light module can be installed easier on the vehicle, because the plug is an integral component of the light module and does not need to be threaded separately through an opening in the bodywork, such as a door or similar part.

Furthermore, it is possible that the plug can be used to fasten the light module on the assembly component by means of holders. Consequently, the purpose of the plug is not only to supply the light module with electrical energy, but the plug can at the same time be used for fastening the light module on the assembly component. The corresponding holders can be equipped with latches or clips which work together with corresponding counterpieces on the assembly component.

Furthermore, the entire light module can be clipped onto the assembly component by means of a latch connector. As a result, the light module can be attached to the assembly component in a particularly simple manufacturing step. Optionally or additionally, the light module can be permanently joined to the assembly component with a screwed connection. Furthermore, it is conceivable that the light module is attached by means of a welded connection, in particular a spot welded connection. Furthermore, a fastening strap can be arranged on the light module which is used to fasten it on the assembly component.

Advantageously, the plug on the light module is designed as a jack which can be connected with the male plug in the vehicle. For this purpose, in particular a latch connector can be provided to join the two parts of the plug. Obviously, it is also possible to design the plug on the light module as a male plug. Additionally, the plug is equipped with reverse connection protection to make sure that the jack and the male plug can only be connected in one position to establish the electrical contact between the light module and the electrical system in the vehicle. At the same time, said reverse connection protection can be integrated with the latch. Said latch connector can comprise for instance a clip or bayonet catch.

Furthermore, it is conceivable that the plug of the light module rests on a bearing bracket of an assembly component designed as a door handle, in particular an exterior door handle and the other main part of the light module is arranged on the inside of the grip of the exterior door handle. For this purpose, the case of the light module can be designed in L-shape and be embedded into notably an L-shaped recess on the assembly component which can be designed as a door handle. As a result, the plug can be positioned in an easily accessible position to achieve a simple connection with the plug inside the vehicle. In so doing, it is particularly advantageous if the plug can protrude through an opening in the bodywork when the assembly component is installed on the vehicle in order to connect it with the counterpiece of the vehicle.

Furthermore, it has been shown to be advantageous if the case of the light module can be manufactured by means of an injection molding procedure, in particular a plastic injection molding procedure. As mentioned earlier, this helps simplify and design the manufacturing process of the light module more economically. What's more, no protruding electrical wires between the light module and the plug are required. Furthermore, it has been shown to be particularly advantageous if the case of the light module comprises translucent materials. Said translucent materials can in particular be a synthetic material, for instance in the form of polycarbonate such as MAKROLON polycarbonate. As a result, the entire case is designed translucent and even the plug can be made of said translucent material. However, to prevent the uncontrolled loss of light emitted by the lamp in the light module, at least one optical lens for a light beam of the lamp can be provided to focus or scatter said light beam, if necessary. In the process, it is particularly advantageous if the provided lens is also designed as a single piece with the case of the light module. This allows the manufacture of the case with the lens and the plug for the light module in a single manufacturing step. Obviously, it is also possible that a plurality of lenses can be arranged in the light module. The lenses can have different lens shapes, such as for example convex or concave lenses. As a result, said lenses can generate a wide-spread beam or a directional beam.

Furthermore, a semi-translucent layer can be provided within the light module to divide the light beam of the lamp, namely into a light beam passing though the semi-translucent layer and another light beam reflected to a different direction on the semi-translucent layer. This makes it possible that the light beam emitted from only one lamp emerges from the light module in at least two different directions, in particular directions offset by 60° and 120°.

The light module according to the invention can be designed with exactly one lamp. Said lamp can be a LED in particular emitting white light. Nevertheless, it is conceivable that the light beam of the lamp is emitted on different sides of the light module. The previously mentioned lenses can be used for this purpose to divide the light beam where it is also possible to use reflective areas to divert part of the light beam. Obviously, it is also possible that a plurality of lamps can be arranged in the light module to obtain a higher light intensity. Furthermore, it is conceivable that the white light is generated by an RGB or LED component so that the red, the green and the blue lights overlap in such a way that white light is generated. A common LED or an OLED (organic LED) can be used as lamp, which can in particular have a large size. As mentioned previously, it is also possible to use a plurality of lamps in the form of LEDs within the light module. In so doing, lamps with different emitted colors can be used. As described above, the light module can emit a wide-spread beam with a wide ranging cone of light toward a first side and/or a directional beam with a focused cone of light toward a second side. Obviously, it is also possible that wide-spread beams or directional beams are emitted toward both sides. The emission of light inside the light module on two sides can in particular achieve the cove lighting for a vehicle and/or the illumination of a recess on a door handle etc. Obviously, it is also conceivable that the light beam of the lamp can emerge from the light module on a third side.

Furthermore, it is conceivable that the light module comprises two optically separated windows from which the light beams of the lamp are emitted in particular as directional beams. The light beams can be emitted toward each other through these two windows at an angle between 60° to 120°, preferably between 80° and 100°, particularly preferably about 90°. The two windows on the light module can be obtained with a shield on the exterior assembly component, in particular an exterior door handle. Said shield optically separates the two windows from each other. At the same time, the corresponding shield on the exterior assembly component can also be used as brace for the light module. Behind said brace, the light module can be arranged form-fitting for attachment on the assembly component, in particular an exterior door handle. The two windows on the light module make it possible to direct the light beam specifically to the areas of the vehicle to be illuminated. This can prevent, for instance, that the driver of a following vehicle is blinded by the light module in the darkness. For this purpose, the light beam emitted by the light module is exclusively directed at the grip recess on the vehicle to prevent the exterior door handle from blinding drivers of following vehicles. Furthermore, it is also possible that the light beam is focused only to the bottom of the vehicle which again prevents blinding drivers of following traffic with a high degree of certainty.

Furthermore, according to the invention it can be provided that the assembly component itself is equipped with an electronic unit which is connected to the electronic system of the vehicle by means of a plug. In the process, the plug of the assembly component can be designed as a single part together with the plug of the light module. The two plugs can be connected to a combo plug with an enclosed guide or a clip connector or similar device. Furthermore, it is conceivable that the two plugs form a one piece unit in which for example the electrical wires of the assembly component lead into the plug of the light module. Consequently, only one plug or combo plug needs to be connected with the electrical system of the vehicle when installing the exterior assembly component on the vehicle. This allows a further simplification of the assembly work associated with installing the assembly component on the vehicle.

Furthermore, it is conceivable that a brightness sensor is provided which is used to activate the light module, in particular the lamp, where the brightness sensor is in particular integrated in the light module. This way, the lamp can be activated in such a way that it only turns on when a certain degree of darkness is reached, rather than consuming unnecessary energy at daytime. Obviously, the brightness sensor can also be arranged in the assembly component or in the electronic system of the vehicle to activate the lamp of the light module. However, the activation is particularly simple if the brightness sensor is integrated in the light module and no other activation cable to the electronic system of the vehicle is required.

Additionally, the light module can be provided with a signal connection to a safety system, in particular an access permission system, comprising a mobile ID transmitter for key-less activation of an unlocking and locking procedure of a lock, wherein the light module can be turned on by way of the safety system. In so doing, a data communication between the ID transmitter and the lock can take place in particular for the locking and unlocking procedure and a code can be exchanged, wherein the safety system only activates or turns on the light module after the code has been evaluated positively. An access permission system within the meaning of the invention can be provided as safety system. This helps prevent the light module from unduly turning on and consuming energy if an unauthorized person approaches the vehicle or tries to access the vehicle.

The light module itself can comprise an electronic control system to activate the lamp, where the electronic control system is supplied with electrical energy by way of the plug. Alternatively, the entire electronic control system can be arranged protected inside the light module by means of a seal in the form of a cover and/or with additional sealing compound. The lamp can be activated with the electronic control system by way of pulse-width modulation.

Furthermore, the invention at hand also relates to a manufacturing procedure for an exterior assembly component of a vehicle. The manufacturing procedure according to the invention provides that the light module with associated plug is assembled in a single manufacturing step. As a result, the light module is not attached on the assembly component first before the plug, but these two steps are taking place in exactly one manufacturing step. As well, the case of the light module is produced in a single manufacturing step together with the plug.

BRIEF DESCRIPTION OF THE DRAWINGS

Additional procedures and advantages of the invention can be derived from the claims, the description and drawings below. Moreover, the disclosed characteristics of the device according to the invention equally apply to the method according to the invention and vice versa. Different exemplary embodiments of the invention are illustrated in the drawings. In the process, the characteristics mentioned in the claims and in the description can be essential to the invention individually or in any combination.

DETAILED DESCRIPTION

In the FIGS. 1 to 7, identical technical characteristics of the respective exemplary embodiments are labeled with the same reference signs.

Figure 1:
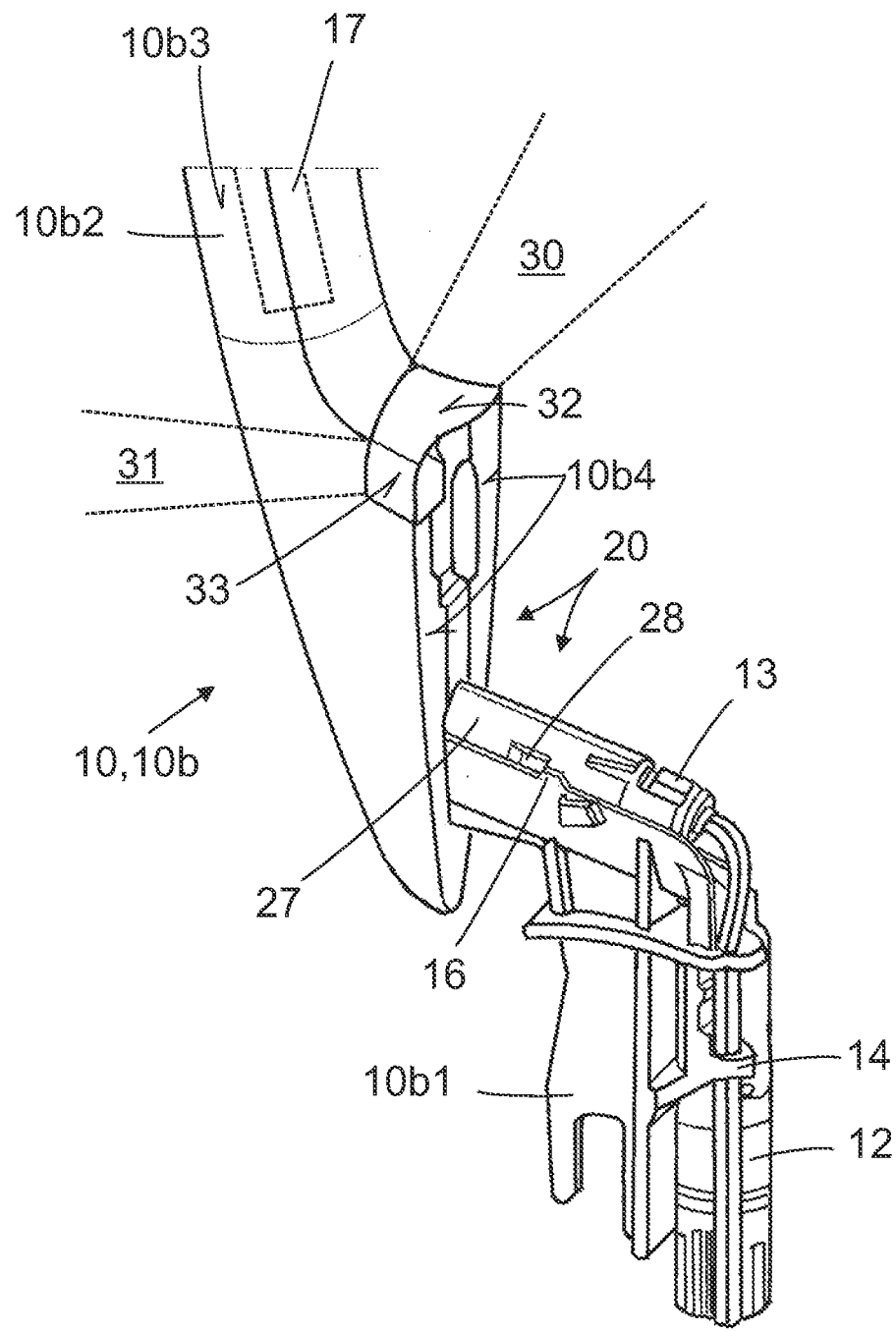
FIG. 1 shows a partially three-dimensional illustration of an assembly component according to the invention in the form of an exterior door handle.

FIG. 1 shows a first exemplary embodiment of the assembly component 10 for a vehicle 100 according to the invention which is normally arranged on the outside of the vehicle 100. A light module 20 is already arranged in a recess 11 on the assembly component 10 of said assembly component 10. The light module 20 is usually installed on the assembly component 10 by simply pushing it into the recess 11, wherein latch connectors are provided to retain the light module 20 permanently joined on the assembly component 10. Said latch connectors can comprise a clip or an enclosed guide. In the presented case, a fastening strap 21.2 provided on the light module 20 can also be used as latch connector. In addition, the light module 20 can be joined with the assembly component 10 by way of a screwed connection or a welded connection. For this purpose, the fastening strap 21.2 contains a bore hole which can be used for the screwed or welded joint. The fastening strap 21.2 itself can slide behind spring-mounted projections arranged on the assembly component 10, thus creating the latch connector 19 mentioned above. Furthermore, a plug 27 designed as a single part with the case 21 of the light module 20 is used to attach the light module 20. For this purpose, protruding retainers 28 in the form of projections are arranged on the plug 27 which work together with the corresponding counterpieces 16 on the exterior assembly component 10 in a form-fitting and/or force-fitting manner. Moreover, the retainers 28 and counterpieces 16 can comprise latch connectors.

Figure 5:
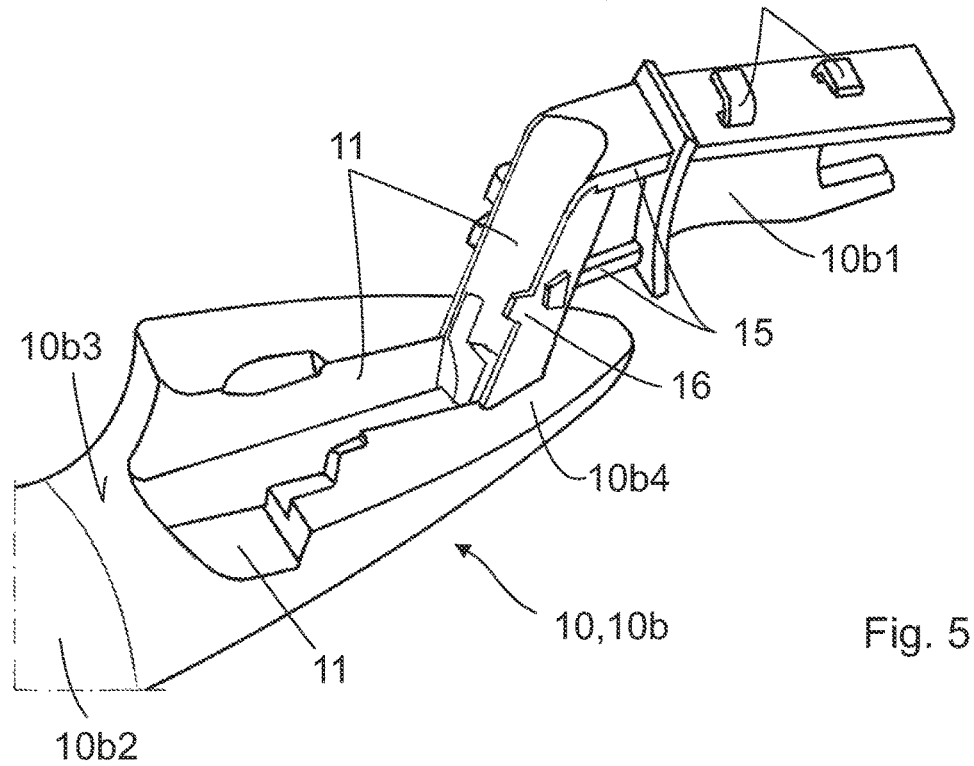
FIG. 5 shows a partially three-dimensional view of the assembly component according to the invention, albeit without an installed light module.

In order to be able to integrate the light module 20 fittingly and unobtrusively in the exterior assembly component 10, the retainer 11 is provided at the back of the assembly component 10 (see FIG. 5). The L-shaped light module 20 is embedded in said retainer 11 in such a way that it creates a flush contact area 10b4 with the assembly component 10. Said contact area 10b4 can be used to attach the assembly component 10 to the vehicle 100. A seal can be arranged between the contact area 10b4 and part of the bodywork of the vehicle 100 which allows the sealing of an opening in the bodywork.

As further illustrated in FIG. 1, the exterior assembly component 10 itself comprises an electronic unit 17 used for instance to operate a safety system of the vehicle 100. Said electronic unit 17 is shown with dashed lines in FIG. 1 and is connected to the electrical system of the vehicle with an additional plug 12. Said plug 12 is mounted on a bearing bracket 10.1 of the exterior door handle 10b. The bearing bracket 10.1 protrudes through an opening in the bodywork of the component 100 and is used for flexibly mounting the door handle 10b. In addition, a mating connector 13 is provided which is connected with the plug 27 of the light module 20 in order to supply the latter with electrical energy. The plug 27 is designed as a jack 27.1 and holds the mating connector 13. In a special variant not illustrated in FIG. 1, the plug 12 and the plug 27 can be designed as a single piece so that both the electronic unit 17 of the assembly component 10 as well as an electronic control system 24 or a lamp 23 can be supplied with electrical energy of the light module 20. To prevent the supply cable of the plug 13 from dangling around loosely, additional fastening hooks 14 arranged offset from each other on the bearing bracket 10b1 of the door handle 10b are provided (see FIG. 5).

Figure 2:
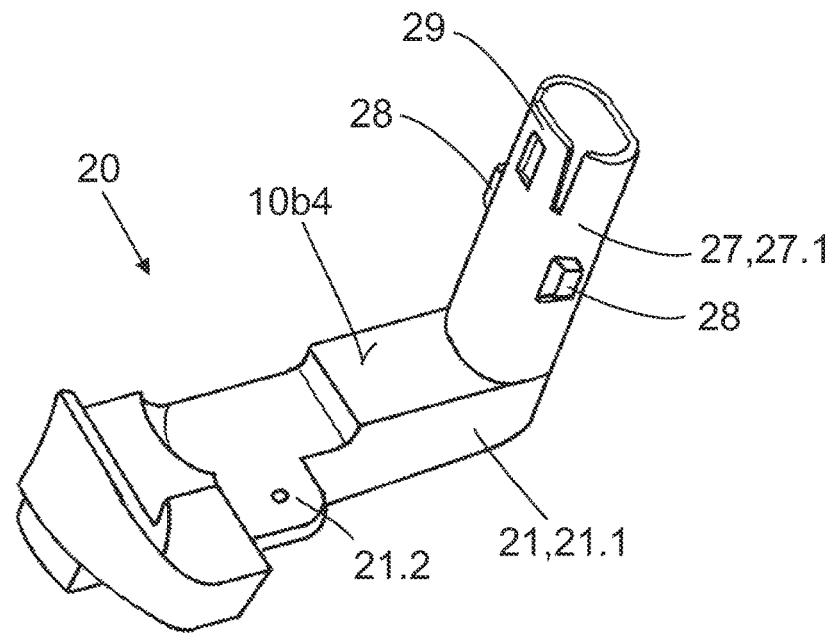
FIG. 2 shows a three-dimensional top view of a light module for the assembly component.

In FIG. 2, the light module 20 is illustrated without the assembly component 10. As is clearly visible, the case 21 comprises a main part 21.1 and the plug 27. In the process, the plug 27 is arranged perpendicular to the main part 21.1 so that the entire case 21 of the light module 20 has an L-shaped design. In order for the plug 27 to have a solid connection with a mating connector 23, a latch connector 29 is provided which is arranged clip-like on the top end of the plug. The clip-like latch connector 29 is created with two cuts in the opening rim of the plug 27 and hence creates a spring-mounted protrusion. At the same time the latch connector 29 serves as reverse connection protection, because it comprises a recess or opening which a protrusion of the plug 13 extends into when the plug 27 is connected to the mating connector 27. The protrusion on the plug 13 ensures that the latter cannot be plugged into the plug 27 the wrong way around. However, at the same time said recess also creates a form closure when the projection is inserted into the opening on the latch connector 29.

Figure 4:
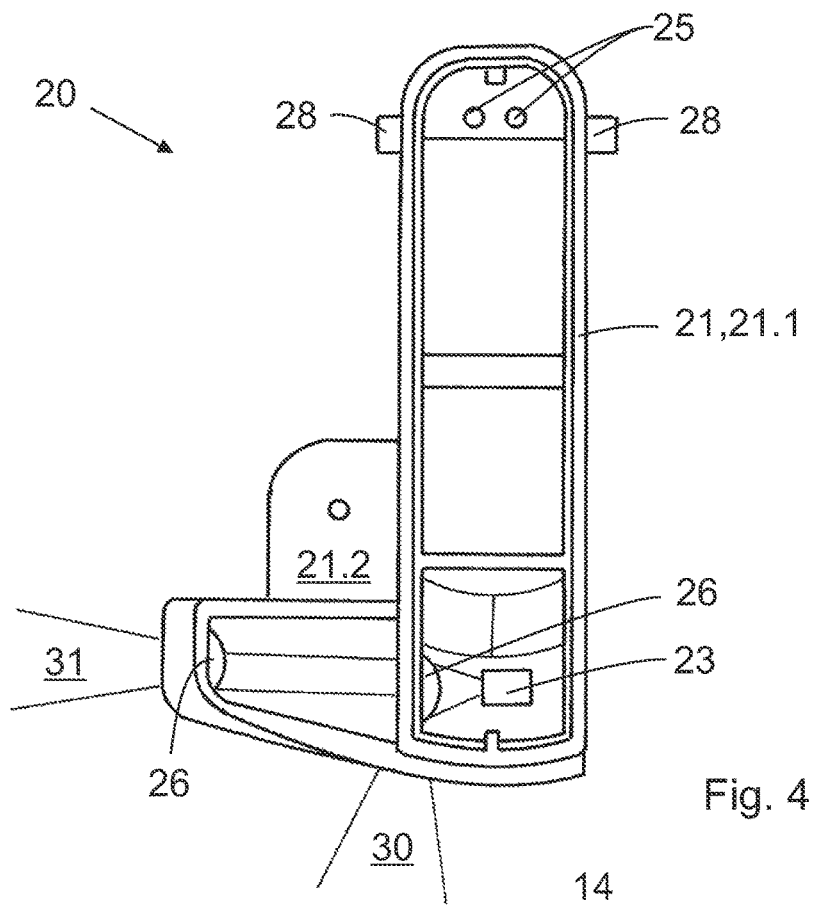
FIG. 4 shows a rear view of the light module illustrated in FIGS. 2 and 3 without the lid.

The entire case 21 of the light module 10 is preferably manufactured by means of a plastic injection molding procedure, wherein in particular a translucent synthetic material in the form of polycarbonate can be used. Consequently, the plug 27 is also designed with the translucent material. Obviously, the transparent surfaces of the light module 20 where no light beams are supposed to be emitted from the lamp 23 can be varnished. The light beams emitted by the lamp 23 emerge from the light module 20 in the form of cones of light 30, 31. In the process, a wide-ranging light beam 30 emerges from a first side 32, which is used to illuminate a recess for an interior area 10b3 of the door handle 10b. In contrast, the cone of light 31 emerges from the second side 33 which is used as cove lighting for the vehicle 100. FIG. 4 illustrates the beam path from the lamp 23 to the cones of light 30, 31 in the case 21 of the light module 20.

Figure 3:
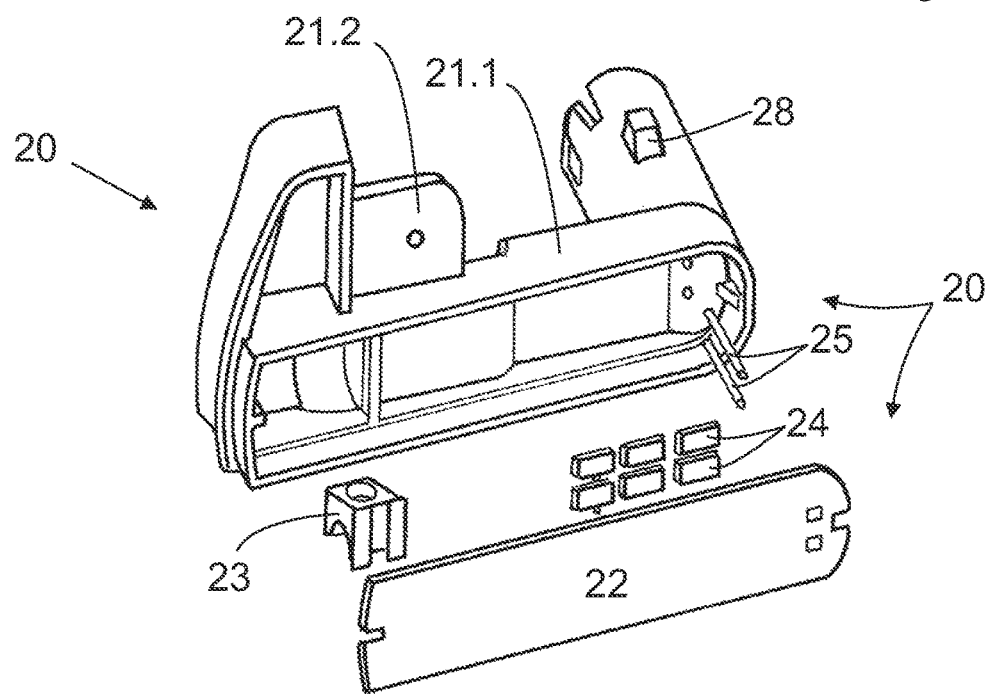
FIG. 3 shows an exploded view of the light module illustrated in FIG. 2.

FIG. 3 shows an exploded view of the light module 20, wherein the corresponding electronic control system 24 and the lamp 23 are also depicted. The electronic control system 24 is arranged on a circuit board 22 which also accommodates the lamp 23. The SMD technology is preferably used for this purpose.

The circuit board 22 can at the same time be used as lid 22 for the case 21 of the light module 20, wherein the circuit board 22 can be connected to the case 21 by means of two connecting rods 25 molded onto the case 21, in particular by means of welded joints. To protect the entire electrical system of the light module 20 from moisture and other environmental elements, it can be sealed with a sealing compound. The circuit board 22 can work together with additional sealing media to seal the case 21. The additionally applied sealing compound provides secure protection against moisture.

FIG. 4 illustrates a rear view of the light module 20, with the lamp 23 drawn in to indicate the beam path of the light in the light module 20. As illustrated, only exactly one lamp 23 is used in the present case which is arranged on the bottom end (relative to FIG. 4) inside the main part 21.1 of the case 21. Said lamp 23 only emits light toward one side, namely toward the left, wherein the emitted light beam hits a first lens 26 with a concave design. A reflective layer is provided behind said lens 26 which divides the light beam for the two cones of light 30 and 31. The cones of light 30, 31 can be designed as a truncated pyramid or a truncated cone. The cone of light 30 emerges wide-ranging from the first side 32 of the case 21, deflected by about 90°. A non-reflected part of the light beam behind the first lens 26 hits a second lens 26 more or less undeflected, where it is partly focused and emerges as a cone of light 31 from the second side 33. In the present exemplary embodiment, the two lenses 26 are designed with identical materials and as a single piece with the case 21 of the light module 20. This allows a particularly simple and economical manufacture of the light module 20, because no additional lenses need to be manufactured and installed.

FIG. 5 again illustrates the L-shaped retainer 11 on the assembly component 10 which is designed as a door handle 10b. In the process, the main part 21.1 of the light module 20 is embedded in an opening of the contact area 10.4 for the retainer 11, which is located at the back of a grip 10b2 of the door handle 10b. In contrast, the plug 27 protruding perpendicular from the main part 21.1 is arranged in the bearing bracket 10b1 or the corresponding retainer area 11. In so doing, the holder 28 of the plug 27 travels behind the counterpiece 16 of the assembly component 10 designed as projection in a form-fitting manner. Furthermore, two fastening hooks 14 are arranged on the back of the bearing bracket 10b1 used to fasten a cable in the vehicle for the mating connector 13. Various reinforcement ledges 15 are provided to increase the stability of the bearing bracket 10b1.

Figure 6:
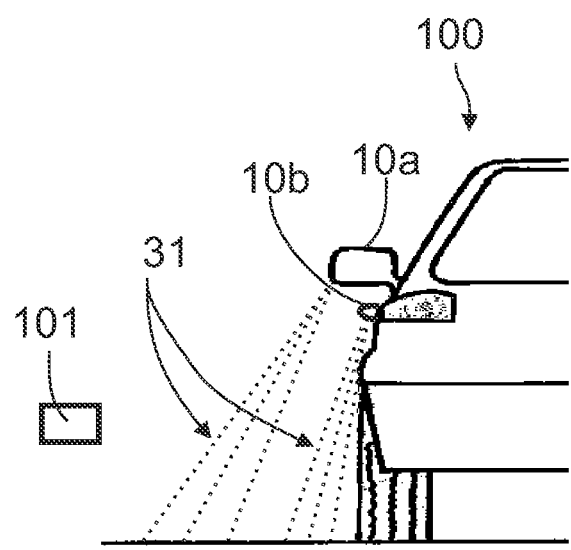
FIG. 6 shows a view of a vehicle having two exterior assembly components in the form of an exterior mirror and an exterior door handle and FIG. 7 shows a partially three-dimensional illustration of an additional assembly component according to the invention in the form of an exterior door handle with a modified light module.

For instance, FIG. 6 illustrates a vehicle 100 in the form of an automobile in which the exterior assembly component 10 is designed as exterior mirror 10a on the one hand and as door handle 10b on the other hand and generates a cove lighting 31, wherein a recess illumination 30 is also conceivable. A signal from an ID transmitter 101 for a safety system, in particular in the form of an access permission system can be used to activate the light module 20 of the vehicle 100. If an authorized person with the corresponding ID transmitter 101 approaches the vehicle 100, the light module 20 can be activated, thus generating the cove lighting 31 provided it is dark enough. Obviously, the light module 20 can also be activated with other systems inside the vehicle.

Figure 7:
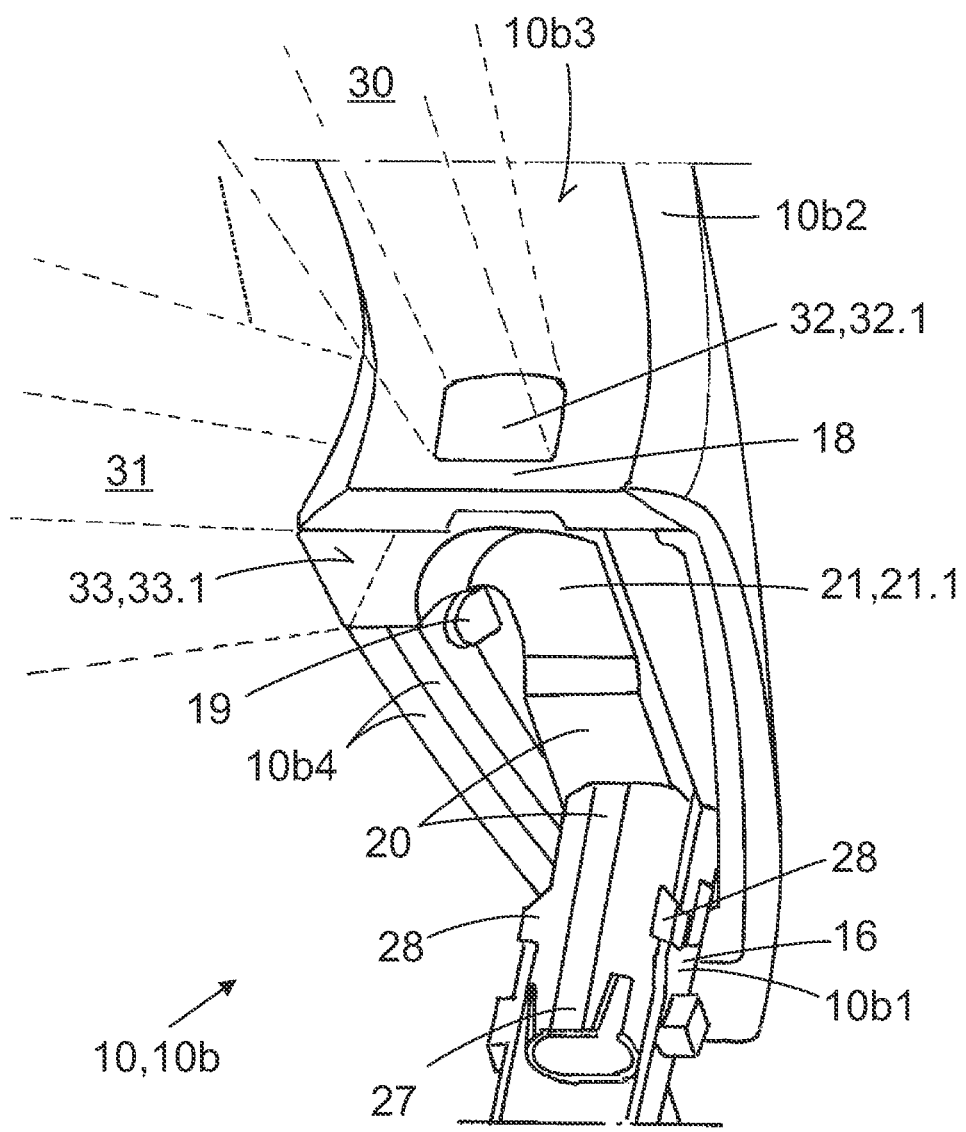

The additional FIG. 7 illustrates a similar exemplary embodiment of the assembly component 10 according to the invention for a vehicle 100 as the one shown in FIG. 1. This exemplary embodiment illustrated in FIG. 7 provides a shield 18 for the corresponding light module 20 on the exterior door handle 10b. In the present example, said shield 18 is at the same time used as additional brace for the light module 20 for mechanically fastening the latter on the exterior door handle 10b. In the process, a first, in particular cuboid window 32.1 of the first side 32 of the light module 20 protrudes through an opening in the exterior door handle 10b which is formed by the shield 18. The light beam of the lamp 23 shines through said first window 32.1 as a cone of light 30 to illuminate the recess. A second window 33.1 is provided in the second side 33 of the light module 20, through which another light beam emerges from the lamp 23 as a cone of light 31 (as cove lighting or floor illumination in front of the vehicle door). As is clearly visible, the light beams emerging from the two windows 32.1 and 33.1 are explicitly directed toward the respective area to be illuminated. For instance, the first window 32.1 is exclusively used to illuminate the recessed grip of the exterior door handle 10b. The second window 33.1 is used to illuminate the floor in front of the vehicle door. The additional shield 18 achieves that the light beams from the lamp 20 are not emitted uncontrolled underneath or above the exterior door handle 10b, which might blind the driver of a following vehicle.

In the exemplary embodiment shown in FIG. 7, the entire light module 20 is fastened undetachably on the exterior door handle 10b by means of the illustrated latch element 19. However, thanks to the available latch connector 19, the light module 20 is arranged reversibly exchangeable on the exterior door handle 10b or the corresponding assembly component 10. Otherwise, the exemplary embodiment shown in FIG. 7 together with the other technical characteristics corresponds to the exemplary embodiment shown in FIG. 1.

With the first window 32.1 it can be achieved that the emitted light beam (cone of light 30) does not extend toward the back at an angle greater than 15°, in particular 10°, measured from the car body to prevent blinding following drivers. As well, the second window 33.1 can be directed toward the floor of the vehicle in such a way that the cone of light 31 equally does not project or radiate away from the car body by more than 15°.

Moreover, we would like to mention that the shield 18 for the optical separation of the two windows 32.1 and 33.1 can also be arranged directly on the light module 20. It can for example be molded on, glued on or applied by way of a printing or varnishing process. In this case however, the shield 18 will not feature a mechanical retaining effect for fastening the light module 20 on the exterior assembly component 10.

The invention claimed is:

1. An exterior assembly for a vehicle, the assembly comprising:
    an exterior door handle;
    a light module having at least one lamp emitting visible light towards an outside of the vehicle, and
    a plug to supply the lamp with electrical energy,
    wherein the light module is a separate component from the door handle and is embedded in a retainer located in a recess within the door handle;
    wherein the plug is designed as a single part,
    wherein the plug is an integral component of a case of the light module and is arranged in the retainer to protrude perpendicularly from the light module, and
    wherein the plug directly attaches the light module to the door handle by means of holders.

2. The exterior assembly according to claim 1, wherein the plug is designed as a single part with the case of the light module.

3. The exterior assembly according to claim 1, wherein the light module is configured to be clip-mounted on the exterior door handle by at least one latch connector.

4. The exterior assembly according to claim 1, wherein the plug comprises a jack which can be connected with a male plug inside the vehicle.

5. The exterior assembly according to claim 4, wherein a plurality of latch connectors are provided for the connection of the jack and the male plug.

6. The exterior assembly according to claim 1, wherein the plug rests on a bearing bracket of the door handle.

7. The exterior assembly according to claim 1, wherein the case of the light module together with the plug is manufactured by way of an injection molding procedure.

8. The exterior assembly according to claim 1, wherein the case of the light module comprises translucent material.

9. The exterior assembly according to claim 1, wherein the case of the light module comprises translucent synthetic material.

10. The exterior assembly according to claim 1, wherein the case of the light module comprises translucent material in the form of polycarbonate.

11. The exterior assembly according to claim 1, wherein the light module comprises at least one optical lens for a light beam of the lamp in order to focus or scatter the light beam.

12. The exterior assembly according to claim 11, wherein the lens is designed as a single part with the case of the light module.

13. The exterior assembly according to claim 1, wherein the light module emits a wide beam with a wide-ranging cone of light toward a first side or a directional beam with a focused cone of light toward a second side.

14. The exterior assembly according to claim 1, wherein the light module emits a wide beam with a wide-ranging cone of light toward a first side or a directional beam with a focused cone of light toward a second side, wherein cove lighting or recess illumination can be achieved.

15. The exterior assembly according to claim 1, further comprising an electronic unit designed with an additional plug and wherein the plug of the light module is designed as a single part with the additional plug of the electronic unit.

16. The exterior assembly according to claim 1, wherein the case of the light module has an L-shaped design.

17. The exterior assembly according to claim 1, wherein the case of the light module has an L-shaped design and is embedded into an L-shaped retainer in the exterior door handle.

18. The exterior assembly according to claim 1, further comprising a brightness sensor which is used to activate the lamp.

19. The exterior assembly according to claim 18, wherein the brightness sensor is integrated in the light module.

20. The exterior assembly according to claim 1, wherein the light module has a signal connection with a security system which comprises a mobile ID transmitter for key-less activation of a locking and unlocking procedure of a lock, wherein the light module can be turned on by way of the security system.

21. The exterior assembly according to claim 20, wherein data communication between the ID transmitter and the lock takes place and a code is exchanged for the locking and unlocking procedure, wherein the safety system only activates the light module after the code has been evaluated.

22. The exterior assembly according to claim 1, wherein an electronic control system is provided in the light module to activate the lamp, wherein the electronic control system is supplied with electrical energy by way of the plug and the electronic control system is arranged inside the light module protected by means of a seal or sealing compound.

23. A manufacturing procedure for the exterior assembly, according to claim 1, having the light module supplied with electrical energy by way of the plug, including a step of simultaneously attaching the light module and the plug on the assembly component.

* * * * *